United States Patent
Jung et al.

(10) Patent No.: US 10,435,390 B2
(45) Date of Patent: Oct. 8, 2019

(54) HETEROCYCLIC COMPOUND AND ORGANIC LIGHT EMITTING DEVICE INCLUDING SAME

(71) Applicant: LG CHEM, LTD., Seoul (KR)

(72) Inventors: Min Woo Jung, Daejeon (KR); Dong Hoon Lee, Daejeon (KR); Jungoh Huh, Daejeon (KR); Boonjae Jang, Daejeon (KR); Minyoung Kang, Daejeon (KR); Dong Uk Heo, Daejeon (KR); Miyeon Han, Daejeon (KR); Wanpyo Hong, Daejeon (KR); Yongha Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 41 days.

(21) Appl. No.: 15/556,465

(22) PCT Filed: Jun. 3, 2016

(86) PCT No.: PCT/KR2016/005885
§ 371 (c)(1),
(2) Date: Sep. 7, 2017

(87) PCT Pub. No.: WO2016/195406
PCT Pub. Date: Dec. 8, 2016

(65) Prior Publication Data
US 2018/0051007 A1    Feb. 22, 2018

(30) Foreign Application Priority Data
Jun. 3, 2015   (KR) .................. 10-2015-0078805

(51) Int. Cl.
*C07D 403/10* (2006.01)
*C07D 401/14* (2006.01)
(Continued)

(52) U.S. Cl.
CPC ......... *C07D 403/10* (2013.01); *C07D 239/26* (2013.01); *C07D 239/28* (2013.01);
(Continued)

(58) Field of Classification Search
None
See application file for complete search history.

(56) References Cited

U.S. PATENT DOCUMENTS

| | | |
|---|---|---|
| 5,759,443 A | 6/1998 | Funfschilling et al. |
| 2014/0231769 A1 | 8/2014 | Nishimura et al. |

(Continued)

FOREIGN PATENT DOCUMENTS

| | | |
|---|---|---|
| CN | 104276997 A | 1/2015 |
| DE | 240887 A1 | 11/1986 |

(Continued)

OTHER PUBLICATIONS

Shibuya: "The Reaction of 2,4,6-Triphenyl-1,3,5-thiadiazin-1-ium Salt with Active Methylene Compounds", The Bulletin of the Chemical Society of Japan, vol. 55, No. 7, 1982, pp. 2158-2160.

(Continued)

*Primary Examiner* — Jay Yang
(74) *Attorney, Agent, or Firm* — Dentons US LLP

(57) ABSTRACT

The present specification relates to a hetero-cyclic compound and an organic light emitting device comprising the same.

13 Claims, 1 Drawing Sheet

(51) Int. Cl.

| | | |
|---|---|---|
| *C07D 239/26* | (2006.01) | |
| *C09K 11/06* | (2006.01) | |
| *H01L 51/00* | (2006.01) | |
| *C07D 239/28* | (2006.01) | |
| *C07D 405/10* | (2006.01) | |
| *C07D 409/10* | (2006.01) | |
| *H01L 51/50* | (2006.01) | |

(52) U.S. Cl.
CPC ......... *C07D 401/14* (2013.01); *C07D 405/10* (2013.01); *C07D 409/10* (2013.01); *C09K 11/06* (2013.01); *H01L 51/0067* (2013.01); *H01L 51/0072* (2013.01); *H01L 51/0073* (2013.01); *H01L 51/0074* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1062* (2013.01); *C09K 2211/1066* (2013.01); *C09K 2211/1088* (2013.01); *C09K 2211/1092* (2013.01); *H01L 51/006* (2013.01); *H01L 51/0094* (2013.01); *H01L 51/5072* (2013.01); *H01L 51/5076* (2013.01); *H01L 51/5092* (2013.01)

(56) References Cited

U.S. PATENT DOCUMENTS

| | | |
|---|---|---|
| 2014/0323723 A1 | 10/2014 | Ahn et al. |
| 2014/0367656 A1 | 12/2014 | Kim et al. |
| 2016/0093812 A1 | 3/2016 | Stoessel et al. |
| 2017/0301866 A1 | 10/2017 | Heo et al. |
| 2018/0170914 A1* | 6/2018 | Miyata ................. C07D 401/14 |
| 2018/0269402 A1 | 9/2018 | Huh et al. |

FOREIGN PATENT DOCUMENTS

| | | |
|---|---|---|
| JP | 2004-031004 A | 1/2004 |
| JP | 2008-006336 A | 1/2008 |
| JP | 2014-157947 A | 8/2014 |
| JP | 2014-531420 A | 11/2014 |
| JP | 2015-504600 A | 2/2015 |
| JP | 2017-533893 A | 11/2017 |
| JP | 2017-535071 A | 11/2017 |
| KR | 2014-0087646 A | 7/2014 |
| WO | 2013/032297 A1 | 3/2013 |
| WO | 2014/166586 A1 | 10/2014 |
| WO | WO-2016/181846 A1 * | 11/2016 |

OTHER PUBLICATIONS

Abd-Elfattah, et al.: "Reactions with alfa-substituted Cinnamonitriles, A Novel Synthesis of Arylpyrimidines", Tetrahedron, vol. 39, No. 19, 1983, pp. 3197-3199.

Zeitschrift fuer Chemie, vol. 25, No. 4, 1985, p. 141.

Sarkar, et al.: "Studies on beta-Enaminonitriles: Part I—Benzoylation in Presence of Sodium in Benzene", Indian Journal of Chemistry, Section B: Organic Chemistry Including Medicinal Chemistry, 125B(11), 986, pp. 1133-1137.

Sibuya, I. et al. "A Method of Synthesizing Pyrimidine Derivatives. II", Bulletin of the Chemical Society of Japan,1973, vol. 46, No. 12, pp. 3902-3903.

Achelle et al. "Pyrimidine Ring as Building Block for the Synthesis of Functionalized Π-Conjugated Materials", Current Organic Synthesis, 2011, vol. 8, No. 6, pp. 1-25.

* cited by examiner

[Figure 1]
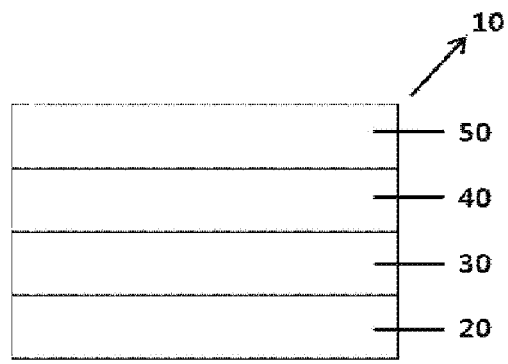
[Figure 2]
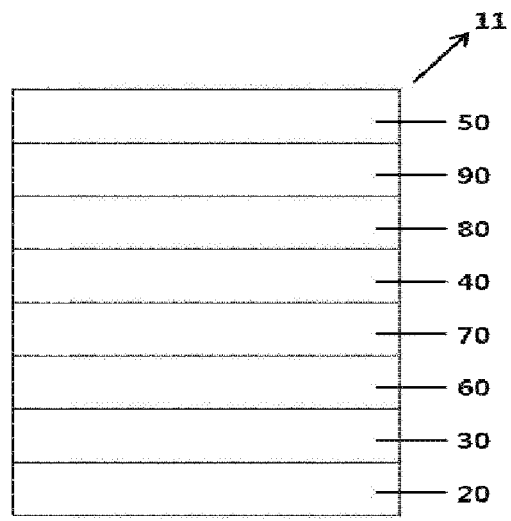

HETEROCYCLIC COMPOUND AND ORGANIC LIGHT EMITTING DEVICE INCLUDING SAME

TECHNICAL FIELD

This application is a National Stage Entry of International Application No. PCT/KR2016/005885 filed on Jun. 3, 2016, and claims the benefit of Korean Application No. 10-2015-0078805 filed on Jun. 3, 2015, all of which are hereby incorporated by reference in their entirety for all purposes as if fully set forth herein.

The present specification relates to a hetero-cyclic compound and an organic light emitting device comprising the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multilayered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

International Publication No. WO2003-012890

DISCLOSURE

Technical Problem

The present specification provides a hetero-cyclic compound and an organic light emitting device comprising the same.

Technical Solution

An exemplary embodiment of the present application provides a hetero-cyclic compound represented by the following Chemical Formula 1.

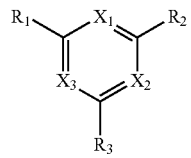

[Chemical Formula 1]

In Chemical Formula 1, $X_1$ to $X_3$ are the same as or different from each other, and are each independently N or C—CN, two of $X_1$ to $X_3$ are N, and $R_1$ to $R_3$ are the same as or different from each other, and are each independently selected from the group consisting of hydrogen; a substituted or unsubstituted straight-chained or branched alkyl group having 1 to 30 carbon atoms; a substituted or unsubstituted monocyclic or polycyclic cycloalkyl group having 3 to 30 carbon atoms; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted arylphosphine group; a substituted or unsubstituted phosphine oxide group; a substituted or unsubstituted monocyclic or polycyclic aryl group having 6 to 30 carbon atoms; and a substituted or unsubstituted monocyclic or polycyclic hetero-cyclic group having 2 to 30 carbon atoms.

Further, an exemplary embodiment of the present specification provides an organic light emitting device including: a first electrode; a second electrode provided to face the first electrode; and one or more organic material layers provided between the first electrode and the second electrode, in which one or more layers of the organic material layers include the above-described hetero-cyclic compound.

Advantageous Effects

A compound according to an exemplary embodiment of the present specification may be used as a material for an organic material layer of an organic light emitting device, and it is possible to improve efficiency, achieve low driving voltage, and/or improve service life characteristics in the organic light emitting device by using the same.

DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

MODE FOR INVENTION

Hereinafter, the present specification will be described in more detail.

The present specification provides a hetero-cyclic compound represented by Chemical Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, examples of the substituents will be described below, but the substituents are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In the present specification,

means a moiety bonded to another substituent or a binding portion.

In the present specification, the halogen group may be fluorine, chlorine, bromine, or iodine.

In the present specification, the number of carbon atoms of an imide group is not particularly limited, but is preferably 1 to 30. Specifically, the imide group may be a compound having the following structures, but is not limited thereto.

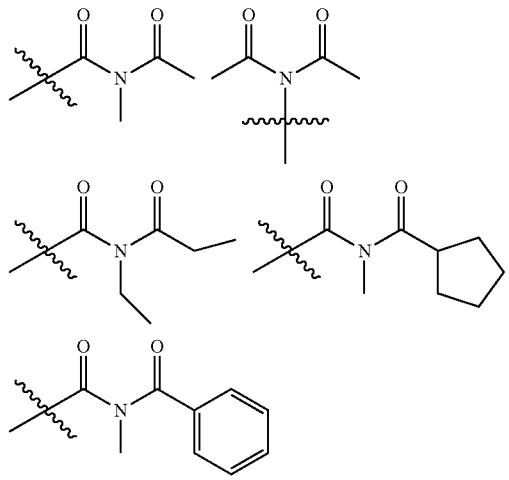

In the present specification, for the amide group, the nitrogen of the amide group may be substituted with hydrogen, a straight-chained, branched, or cyclic alkyl group having 1 to 30 carbon atoms, or an aryl group having 6 to 30 carbon atoms. Specifically, the amide group may be a compound having the following structural formulae, but is not limited thereto.

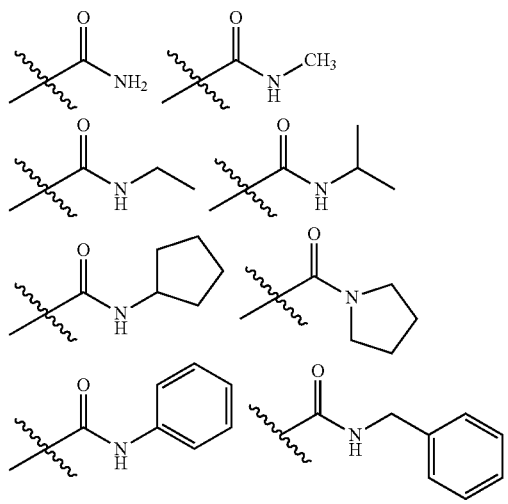

In the present specification, the number of carbon atoms of a carbonyl group is not particularly limited, but is preferably 1 to 30. Specifically, the carbonyl group may be a compound having the following structures, but is not limited thereto.

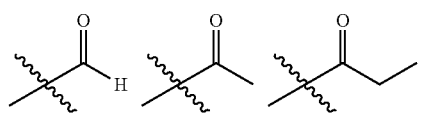

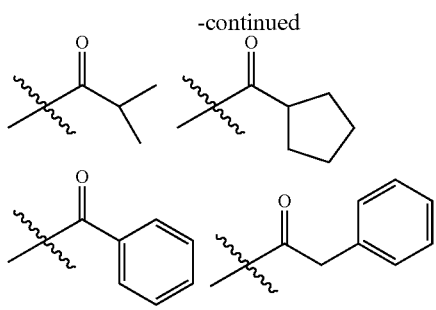

In the present specification, in an ester group, the oxygen of the ester group may be substituted with a straight-chained, branched, or cyclic alkyl group having 1 to 25 carbon atoms, or an aryl group having 6 to 30 carbon atoms. Specifically, the ester group may be a compound having the following structural formulae, but is not limited thereto.

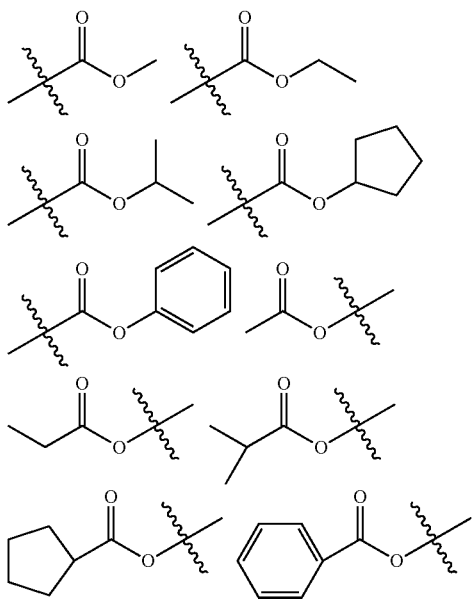

In the present specification, the alkyl group may be straight-chained or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 30, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the amine group may be selected from the group consisting of —NH2; an alkylamine group; an aralkylamine group; an arylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group.

In the present specification, the alkyl group in the alkylamine, the aralkylamine, the alkylthioxy group, and the alkylsulfoxy group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but are not limited thereto.

In the present specification, the alkenyl group may be straight-chained or branched, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the boron group may be —$BR_{100}R_{101}$, and $R_{100}$ and $R_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight-chained or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituent groups may combine with each other to form a ring.

When the fluorenyl group is substituted, the fluorenyl group may be

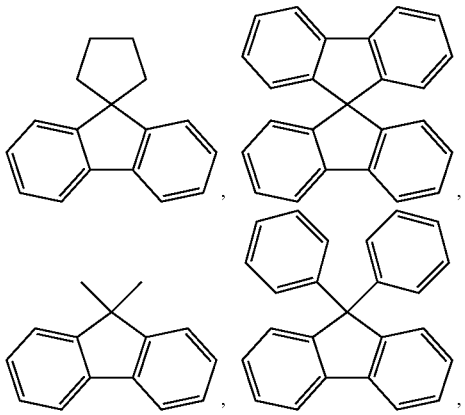

and the like. However, the fluorenyl group is not limited thereto.

In the present specification, the aryl group in the aryloxy group, the arylthioxy group, the arylsulfoxy group, and the aralkylamine group is the same as the above-described example of the aryl group. Specifically, examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but are not limited thereto.

In the present specification, the heteroaryl group includes one or more of an atom other than carbon, that is, a heteroatom, and specifically, the heteroatom may include one or more atoms selected from the group consisting of O, N, Se, S, and the like. The number of carbon atoms thereof is not particularly limited, but is preferably 2 to 30. Examples of the hetero-cyclic group include a thiophene group, a furanyl group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the heteroaryl in the heteroarylamine group may be selected from the above-described examples of the heteroaryl group.

According to an exemplary embodiment of the present specification, the hetero-cyclic compound represented by Chemical Formula 1 may be represented by the following Chemical Formula 2 or 3.

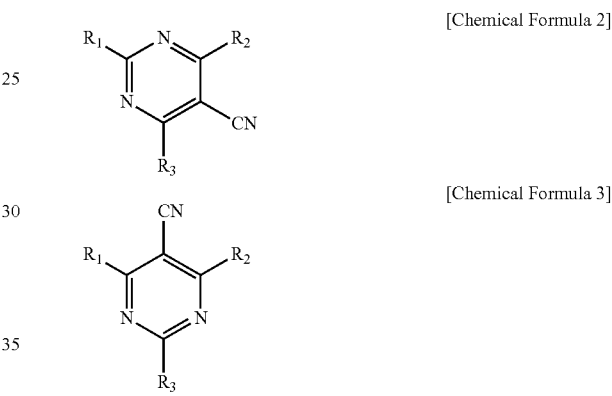

[Chemical Formula 2]

[Chemical Formula 3]

In Chemical Formulae 2 and 3, the definitions of $R_1$ to $R_3$ are the same as those defined in Chemical Formula 1.

According to an exemplary embodiment of the present specification, in Chemical Formula 1, $R_1$ to $R_3$ are the same as or different from each other, and are each independently a substituted or unsubstituted monocyclic or polycyclic aryl group having 6 to 20 carbon atoms.

According to an exemplary embodiment of the present specification, $R_1$ to $R_3$ are the same as or different from each other, and are each independently selected from the group consisting of a substituted or unsubstituted phenyl group; a substituted or unsubstituted biphenyl group; a substituted or unsubstituted terphenyl group; and a substituted or unsubstituted fluorenyl group.

According to an exemplary embodiment of the present specification, $R_1$ to $R_3$ are the same as or different from each other, and are each independently selected from the group consisting of a phenyl group which is unsubstituted or substituted with a carbazolyl group, a dibenzofuranyl group, or a dibenzothiophene group; a biphenyl group which is unsubstituted or substituted with a carbazolyl group; a terphenyl group which is unsubstituted or substituted with a pyridyl group; and a fluorenyl group which is unsubstituted or substituted with a phenyl group.

According to an exemplary embodiment of the present specification, $R_1$ to $R_3$ are the same as or different from each other, and are each independently selected from the group consisting of a phenyl group which is unsubstituted or substituted with a carbazolyl group, a dibenzofuranyl group, or a dibenzothiophene group; a biphenyl group which is substituted with a carbazolyl group; a terphenyl group which is substituted with a pyridyl group; and a fluorenyl group which is substituted with a phenyl group.

According to an exemplary embodiment of the present specification, $R_1$ and $R_2$ are the same as or different from each other, and are each independently a substituted or unsubstituted phenyl group.

According to an exemplary embodiment of the present specification, $R_1$ and $R_2$ are a phenyl group.

According to an exemplary embodiment of the present specification, $R_3$ is selected from the group consisting of a substituted or unsubstituted phenyl group; a substituted or unsubstituted biphenyl group; a substituted or unsubstituted terphenyl group; and a substituted or unsubstituted fluorenyl group.

According to an exemplary embodiment of the present specification, $R_3$ is selected from the group consisting of a phenyl group which is unsubstituted or substituted with a carbazolyl group, a dibenzofuranyl group, or a dibenzothiophene group; a biphenyl group which is unsubstituted or substituted with a carbazolyl group; a terphenyl group which is unsubstituted or substituted with a pyridyl group; and a fluorenyl group which is unsubstituted or substituted with a phenyl group.

According to an exemplary embodiment of the present specification, $R_3$ is selected from the group consisting of a phenyl group which is substituted with a carbazolyl group, a dibenzofuranyl group, or a dibenzothiophene group; a biphenyl group which is substituted with a carbazolyl group; a terphenyl group which is substituted with a pyridyl group; and a fluorenyl group which is substituted with a phenyl group.

According to an exemplary embodiment of the present specification, the hetero-cyclic compound represented by Chemical Formula 1 is any one of the following Compounds 1 to 9.

Compound 1

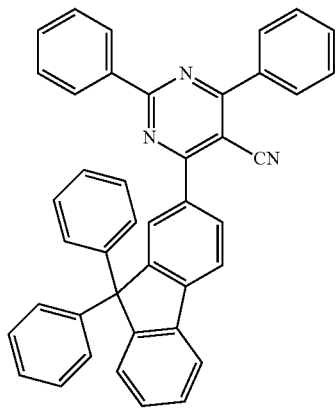

Compound 2

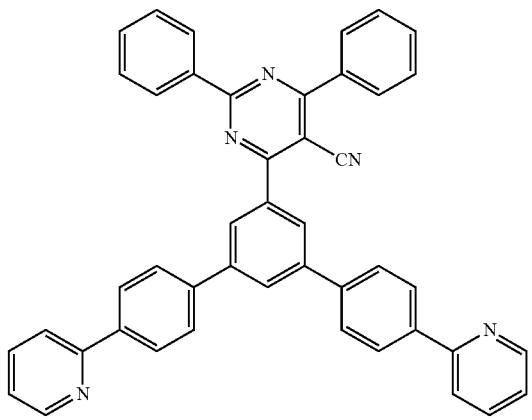

Compound 3

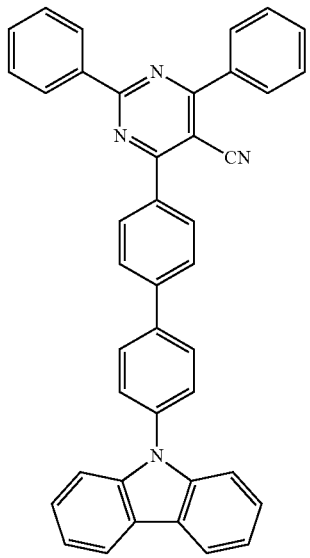

Compound 4

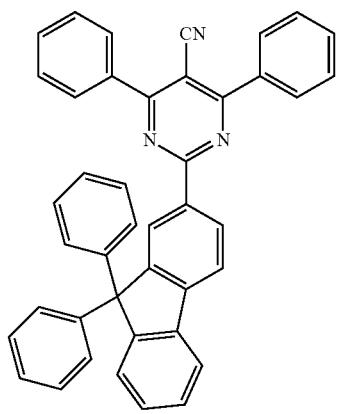

-continued

Compound 5
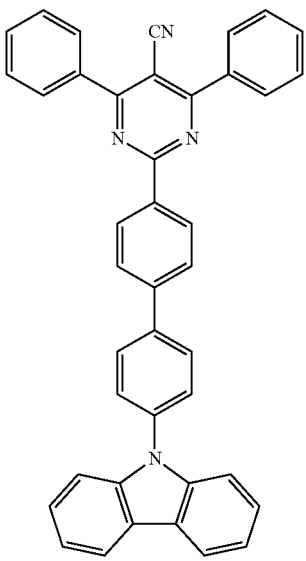

Compound 6
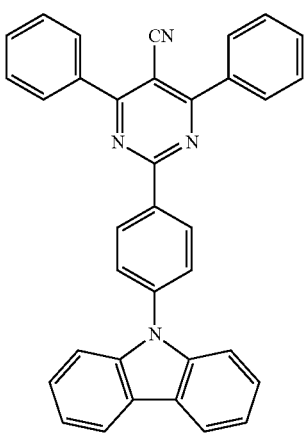

Compound 7
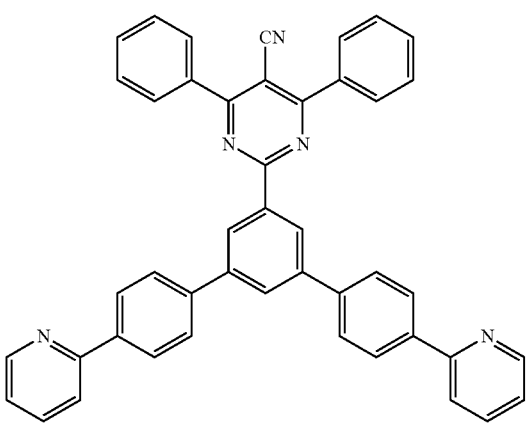

-continued

Compound 8
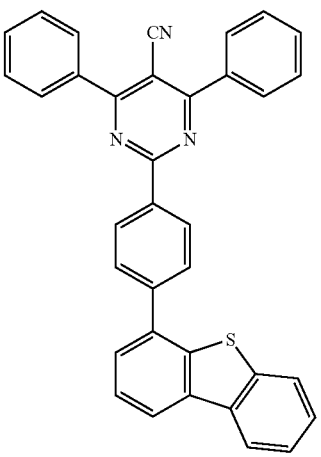

Compound 9
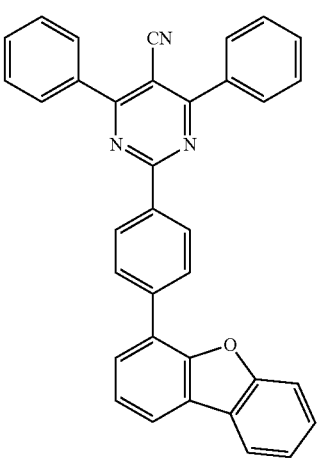

An exemplary embodiment of the present specification provides an organic light emitting device including: a first electrode; a second electrode provided to face the first electrode; and one or more organic material layers provided between the first electrode and the second electrode, in which one or more layers of the organic material layers include the above-described hetero-cyclic compound.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transporting layer, an electron blocking layer, a light emitting layer, a hole blocking layer, an electron transporting layer, an electron injection layer, and the like as organic material layers. However, the structure of the organic light emitting device is not limited thereto, and may include a fewer number of organic layers.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transporting layer 70, a light emitting layer 40, an electron transporting layer 80, an electron injection layer 90, and a second electrode 50 are sequentially stacked on a substrate 20. FIG. 2 is an exemplified structure according to exemplary embodiments of the present specification, and may further include other organic material layers.

According to an exemplary embodiment of the present specification, the organic material layer includes a light emitting layer, and the light emitting layer includes the hetero-cyclic compound represented by Chemical Formula 1.

According to an exemplary embodiment of the present specification, the light emitting layer includes the hetero-cyclic compound represented by Chemical Formula 1 as a host.

According to an exemplary embodiment of the present specification, the organic material layer includes an electron transporting layer or an electron injection layer, and the electron transporting layer or the electron injection layer includes the hetero-cyclic compound represented by Chemical Formula 1.

According to an exemplary embodiment of the present specification, the organic material layer includes an electron transporting layer, an electron injection layer, or a layer which simultaneously transports and injects electrons, and the electron transporting layer, the electron injection layer, or the layer which simultaneously transports and injects electrons includes the hetero-cyclic compound represented by Chemical Formula 1.

According to an exemplary embodiment of the present specification, the organic material layer includes a light emitting layer, and the light emitting layer includes a compound represented by the following Chemical Formula 1-A.

[Chemical Formula 1-A]

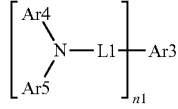

In Chemical Formula 1-A, n1 is an integer of 1 or more,

Ar3 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L1 is a direct bond; a substituted or unsubstituted arylene group; or a substituted or unsubstituted heteroarylene group, Ar4 and Ar5 are the same as or different from each other, and are each independently a substituted or unsubstituted aryl group; a substituted or unsubstituted silyl group; a substituted or unsubstituted alkyl group; a substituted or unsubstituted arylalkyl group; or a substituted or unsubstituted heteroaryl group, or may combine with each other to form a substituted or unsubstituted ring, and when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, L1 is a direct bond.

According to an exemplary embodiment of the present specification, n1 is 2.

In an exemplary embodiment of the present specification, Ar3 is a divalent pyrene group which is unsubstituted or substituted with deuterium, a methyl group, an ethyl group, an isopropyl group, or a tert-butyl group; or a divalent chrysene group which is unsubstituted or substituted with deuterium, a methyl group, an ethyl group, or a tert-butyl group.

According to an exemplary embodiment of the present specification, Ar4 and Ar5 are the same as or different from each other, and are each independently a substituted or unsubstituted aryl group having 6 to 30 carbon atoms.

According to an exemplary embodiment of the present specification, Ar4 and Ar5 are the same as or different from each other, and are each independently an aryl group which is unsubstituted or substituted with a silyl group which is substituted with a methyl group, an ethyl group, an isopropyl group, a tert-butyl group, a nitrile group, or an alkyl group.

According to an exemplary embodiment of the present specification, Ar4 and Ar5 are the same as or different from each other, and are each independently an aryl group which is unsubstituted or substituted with a silyl group which is substituted with an alkyl group.

According to an exemplary embodiment of the present specification, Ar4 and Ar5 are the same as or different from each other, and are each independently an aryl group which is unsubstituted or substituted with a trimethylsilyl group.

According to an exemplary embodiment of the present specification, Ar4 and Ar5 are the same as or different from each other, and are each independently a substituted or unsubstituted phenyl group; a substituted or unsubstituted biphenyl group; or a substituted or unsubstituted terphenyl group.

According to an exemplary embodiment of the present specification, Ar4 and Ar5 are the same as or different from each other, and are each independently a phenyl group which is unsubstituted or substituted with a methyl group, an ethyl group, an isopropyl group, a tert-butyl group, a nitrile group, or a trimethylsilyl group.

According to an exemplary embodiment of the present specification, Ar4 and Ar5 are the same as or different from each other, and are each independently a biphenyl group which is unsubstituted or substituted with a methyl group, an ethyl group, a tert-butyl group, a nitrile group, or a trimethylsilyl group.

According to an exemplary embodiment of the present specification, Ar4 and Ar5 are the same as or different from each other, and are each independently a terphenyl group which is unsubstituted or substituted with a methyl group, an ethyl group, a tert-butyl group, a nitrile group, or a trimethylsilyl group.

According to an exemplary embodiment of the present specification, Ar4 and Ar5 are the same as or different from each other, and are each independently a substituted or unsubstituted heteroaryl group having 6 to 30 carbon atoms.

According to an exemplary embodiment of the present specification, Ar4 and Ar5 are the same as or different from each other, and are each independently a heteroaryl group which is unsubstituted or substituted with a silyl group or a phenyl group which is substituted with a methyl group, an ethyl group, a tert-butyl group, a nitrile group, or an alkyl group.

According to an exemplary embodiment of the present specification, Ar4 and Ar5 are the same as or different from each other, and are each independently a dibenzofuran group which is unsubstituted or substituted with a methyl group, an ethyl group, a tert-butyl group, a nitrile group, a trimethylsilyl group, or a phenyl group.
According to an exemplary embodiment of the present specification, Chemical Formula 1-A is selected from the following compounds.
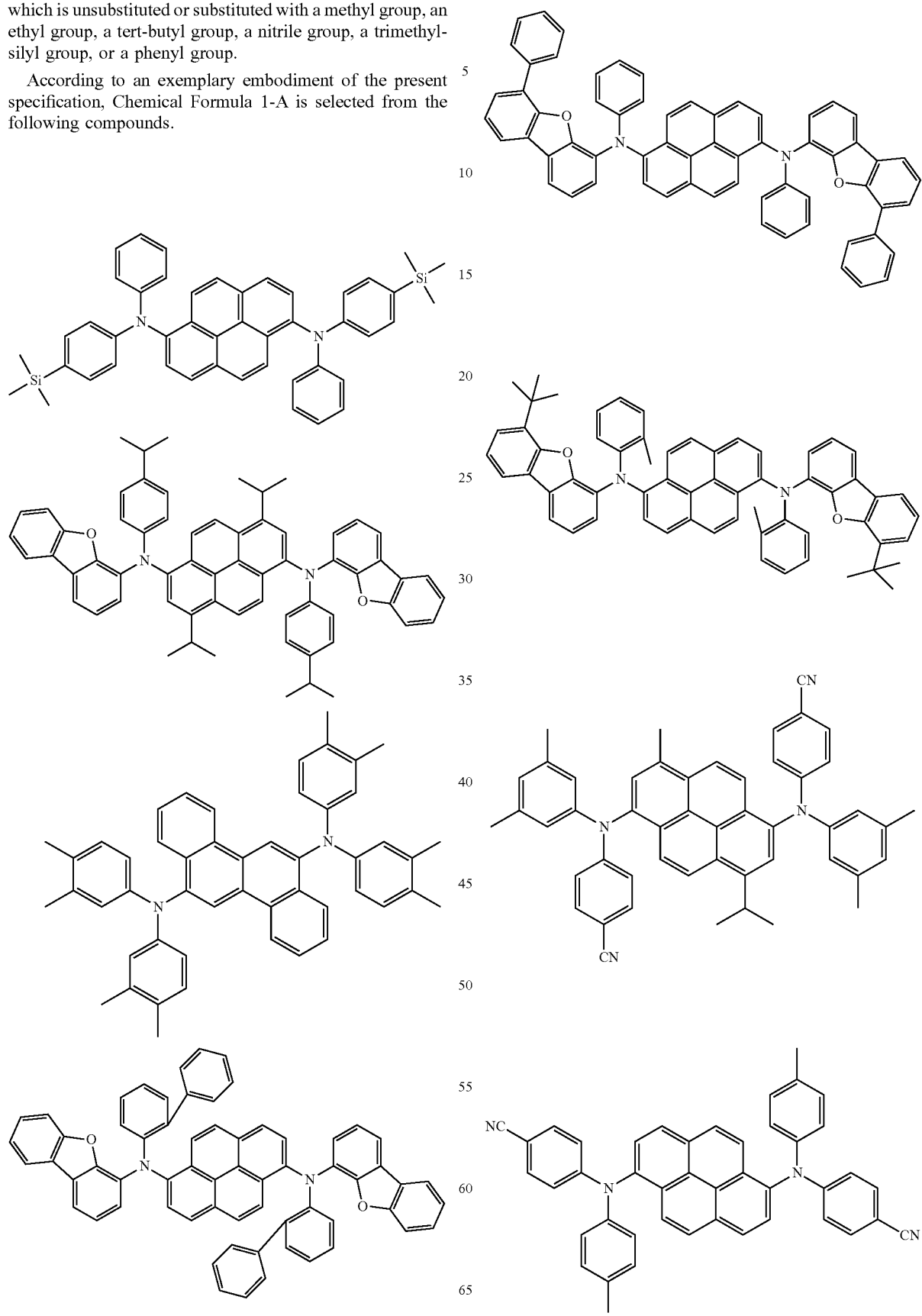

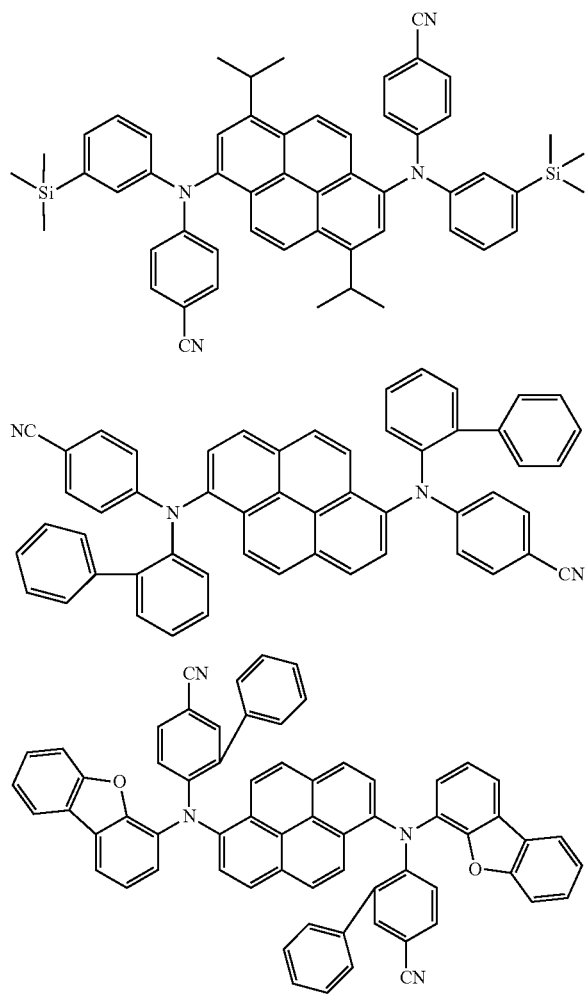

According to an exemplary embodiment of the present specification, the organic material layer includes a light emitting layer, and the light emitting layer includes a compound represented by the following Chemical Formula 2-A.

[Chemical Formula 2-A]

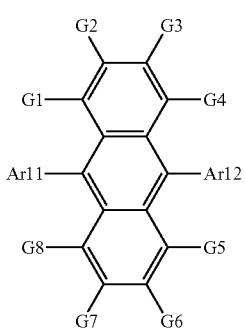

In Chemical Formula 2-A,

Ar11 and Ar12 are the same as or different from each other, and are each independently a substituted or unsubstituted monocyclic aryl group; or a substituted or unsubstituted polycyclic aryl group, G1 to G8 are the same as or different from each other, and are each independently hydrogen; a substituted or unsubstituted monocyclic aryl group; or a substituted or unsubstituted polycyclic aryl group.

According to an exemplary embodiment of the present specification, the organic material layer includes a light emitting layer, and the light emitting layer includes the compound represented by Chemical Formula 2-A as a host of the light emitting layer.

According to an exemplary embodiment of the present specification, Ar11 and Ar12 are the same as or different from each other, and are each independently a substituted or unsubstituted polycyclic aryl group.

According to an exemplary embodiment of the present specification, Ar11 and Ar12 are the same as or different from each other, and are each independently a substituted or unsubstituted polycyclic aryl group having 10 to 30 carbon atoms.

According to an exemplary embodiment of the present specification, Ar11 and Ar12 are the same as or different from each other, and are each independently a substituted or unsubstituted naphthyl group.

According to an exemplary embodiment of the present specification, Ar11 and Ar12 are the same as or different from each other, and are each independently a substituted or unsubstituted 1-naphthyl group.

According to an exemplary embodiment of the present specification, Ar11 and Ar12 are a 1-naphthyl group.

According to an exemplary embodiment of the present specification, G1 to G8 are hydrogen.

According to an exemplary embodiment of the present specification, Chemical Formula 2-A is selected from the following compound.

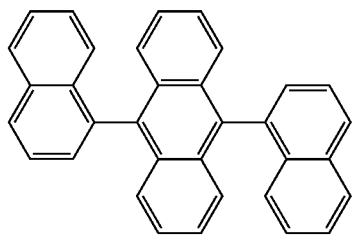 [SMILES: c1ccc2c(-c3c4ccccc4c(-c4cccc5ccccc45)c4ccccc34)cccc2c1]

According to an exemplary embodiment of the present specification, the organic material layer includes a light emitting layer, and the light emitting layer includes the compound represented by Chemical Formula 1-A as a dopant of the light emitting layer, and includes the compound represented by Chemical Formula 2-A as a host of the light emitting layer.

According to an exemplary embodiment of the present specification, the organic material layer may further include one or more layers selected from the group consisting of a hole injection layer, a hole transporting layer, a light emitting layer, an electron transporting layer, and an electron injection layer.

The organic light emitting device of the present specification may be manufactured by the materials and methods known in the art, except that one or more layers of the organic material layers include the hetero-cyclic compound of the present specification, that is, the hetero-cyclic compound represented by Chemical Formula 1.

When the organic light emitting device includes a plurality of organic material layers, the organic material layers may be formed of the same material or different materials.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a first electrode by using a physical vapor deposition (PVD) method such as sputtering or e-beam evaporation, forming an organic material layer including a hole injection layer, a hole transporting layer, a light emitting layer, and an electron transporting layer thereon, and then depositing a material, which may be used as a second electrode, thereon. In addition to the method as described above, an organic light emitting device may be made by sequentially depositing a negative electrode material, an organic material layer, and a first electrode material on a substrate. Further, the hetero-cyclic compound represented by Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly [3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transporting layer is a layer which receives holes from a hole injection layer and transports holes to a light emitting layer, and a hole transporting material is suitably a material which may receive holes from a positive electrode or a hole injection layer to transfer holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material for the light emitting layer is a material which may receive holes and electrons from a hole transporting layer and an electron transporting layer, respectively, and combine the holes and the electrons to emit light in a visible ray region, and is preferably a material having good quantum efficiency to fluorescence or phosphorescence. Specific examples thereof include: a 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specifically, examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a condensed aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting material of the electron transporting layer is a material which receives electrons from an electron injection layer and transports the electrons to a light emitting layer, and the electron transporting material is a material which may inject electrons well from a negative electrode and transfer the electrons to a light emitting layer, and is suitably a material which has large mobility for the electrons. Specific examples thereof include: an Al complex of 8-hydroxyquinoline; a complex including Alq3; an organic radical compound; a hydroxyflavone-metal complex, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the material to be used.

According to an exemplary embodiment of the present specification, the hetero-cyclic compound represented by Chemical Formula 1 may be included in an organic solar cell or an organic transistor in addition to the organic light emitting device.

Hereinafter, the present specification will be described in detail with reference to the Examples for specifically describing the present specification. However, the Examples according to the present specification may be modified in various forms, and it is not interpreted that the scope of the present specification is limited to the Examples described below in detail. The Examples of the present specification are provided for more completely explaining the present specification to the person with ordinary skill in the art.

PREPARATION EXAMPLES

Preparation Example 1. Preparation of Compound 1

(1) Preparation of Compound 1A

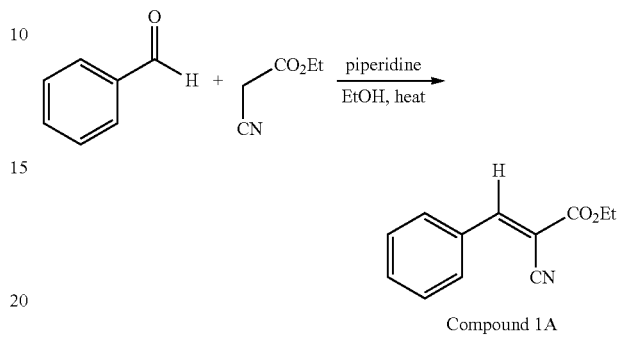

Compound 1A

Benzaldehyde (50 g, 471.16 mmol) and ethyl-2-cyanoacetate (58.6 g, 518.28 mmol) were added to 500 ml of ethanol under nitrogen atmosphere, and then sufficiently stirred, and then piperidine (1.5 g, 18.85 mmol) was slowly added dropwise thereto, and then the resulting mixture was refluxed and stirred for about 12 hours. After the reaction was terminated, the temperature of the mixture was lowered to normal temperature, and then filtered. The filtered material was extracted with chloroform and water, and then the organic layer was dried by using magnesium sulfate. Thereafter, the organic layer was distilled under reduced pressure, and then recrystallized with ethanol to prepare and then dry Compound 1A (80.6 g, 85%).

(2) Preparation of Compound 1B

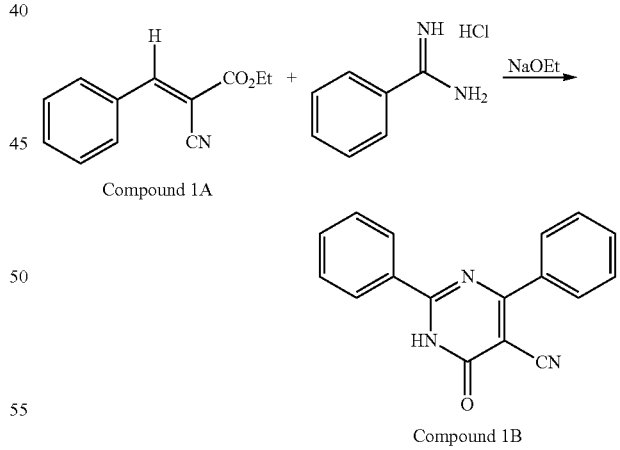

Compound 1B

Compound 1A (80.6 g, 400.49 mmol), benzimidamide hydrochloride (69.9 g, 440.61 mmol), and sodium ethoxide were put into 800 ml of dimethylacetamide, and the resulting mixture was reacted for 4 hours by being stirred and refluxed. After the reaction, the mixture was cooled to normal temperature, and then filtered. The filtered material was sufficiently washed with water and ethanol, and then dried to prepare Compound 1B (84.3 g, 77%).

(3) Preparation of Compound 1C

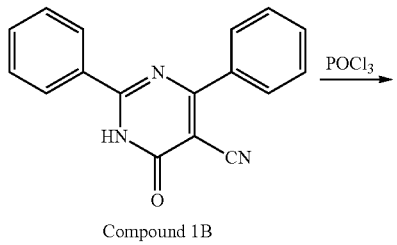

Compound 1B

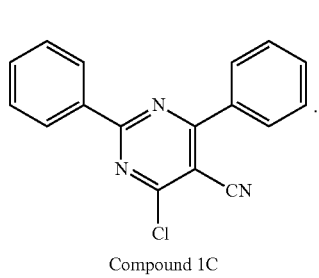

Compound 1C

Compound 1B (84.3 g, 361.38 mmol) was put into an excessive amount of phosphinyl trichloride (POCl₃), and the resulting mixture was refluxed at 120° C. After the mixture was cooled to normal temperature, an ethanol/water mixed solution was introduced into the mixture, and then the resulting mixture was filtered. The filtered solid was slurry treated with acetonitrile, and then the resulting product was again filtered and dried to obtain Compound 1C (63.3 g, 60%).

(4) Preparation of Compound 1

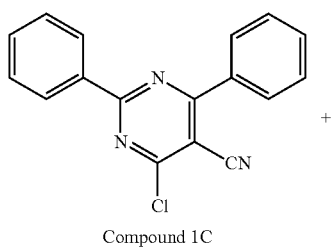

Compound 1C

+

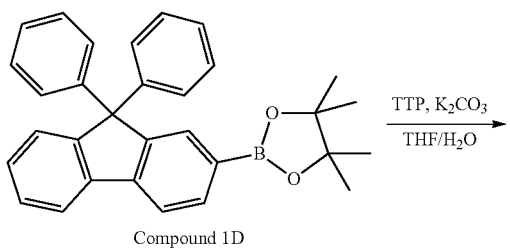

Compound 1D

-continued

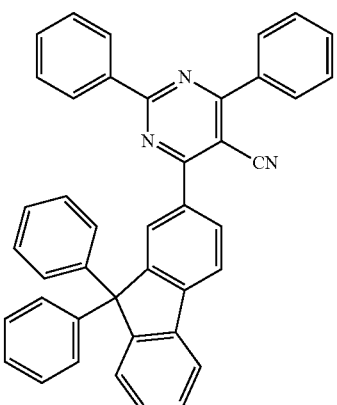

Compound 1

Compound 1C (10.0 g, 34.28 mmol) and Compound 1D (16.8 g, 37.70 mmol) were put into 100 ml of tetrahydrofuran under nitrogen atmosphere, and the resulting mixture was stirred and refluxed. Thereafter, potassium carbonate (14.2 g, 102.83 mmol) was dissolved in 30 ml of water, the resulting solution was introduced thereinto, the resulting mixture was sufficiently stirred, and then tetrakistriphenylphosphinopalladium (1.2 g, 1.03 mmol) was introduced thereinto. After the reaction for 3 hours, the temperature of the mixture was lowered to normal temperature and filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 1 (14.6 g, 74%). Compound 1D was purchased from Aldrich and used.

MS: $[M+H]^+$=573

Preparation Example 2. Preparation of Compound 2

(1) Preparation of Compound 2A

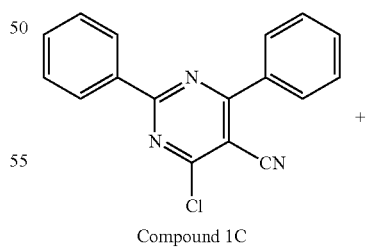

Compound 1C

+

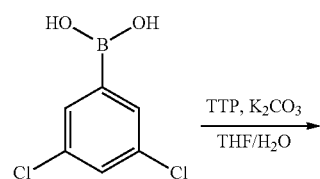

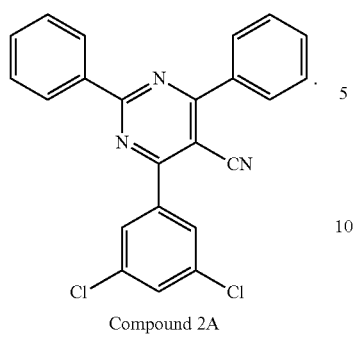

Compound 2A

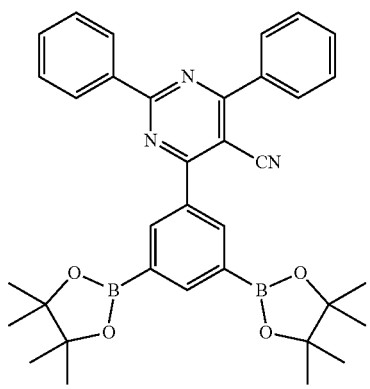

Compound 2B

Compound 1C (20 g, 68.55 mmol) and (3,5-dichlorophenyl)boronic acid (14.4 g, 75.41 mmol) were put into 200 ml of tetrahydrofuran under nitrogen atmosphere, and the resulting mixture was stirred and refluxed. Thereafter, potassium carbonate (28.4 g, 205.66 mmol) was dissolved in 80 ml of water, and the resulting solution was introduced thereinto, the resulting mixture was sufficiently stirred, and then tetrakistriphenyl-phosphinopalladium (2.4 g, 2.06 mmol) was introduced thereinto. After the reaction for 1 hour, the temperature of the mixture was lowered to normal temperature and filtered. The filtered material was extracted with chloroform and water, and then the organic layer was dried by using magnesium sulfate. Thereafter, the organic layer was distilled under reduced pressure, and then recrystallized by using ethanol. The produced solid was filtered and then dried to prepare Compound 2A (27.6 g, 76%).

(2) Preparation of Compound 2B

Compound 2A (21.0 g, 22.2 mmol), bis(pinacolato)diboron (31.8 g, 125.29 mmol), and potassium acetate (30.7 g, 313.21 mol) were mixed under nitrogen atmosphere, and the resulting mixture was added to 200 ml of dioxane, and heated while being stirred. Bis(dibenzylideneacetone)palladium (1.8 g, 3.31 mmol) and tricyclohexylphosphine (1.8 mg, 6.26 mmol) were added to the mixture while being refluxed, and the mixture was heated and stirred for 12 hours. After the reaction was terminated, the temperature of the mixture was lowered to normal temperature, and then filtered. Water was poured into the filtrate, the product was extracted with chloroform, and the organic layer was dried with anhydrous magnesium sulfate. After distillation under reduced pressure, recrystallization was performed with ethanol to prepare Compound 2B (24.4 g, 80%).

(3) Preparation of Compound 2

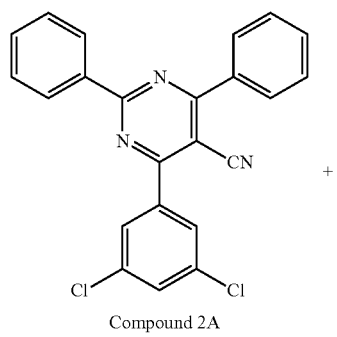

Compound 2A

+

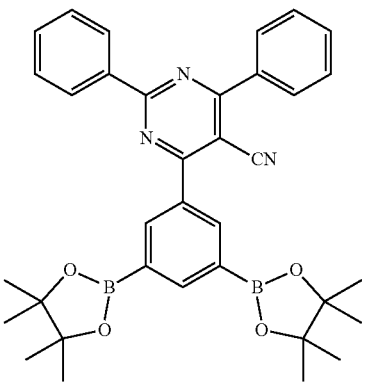

Compound 2B

+

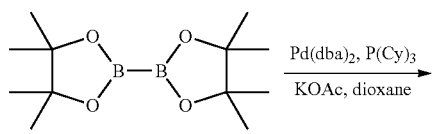

$\xrightarrow{\text{Pd(dba)}_2, \text{P(Cy)}_3}{\text{KOAc, dioxane}}$

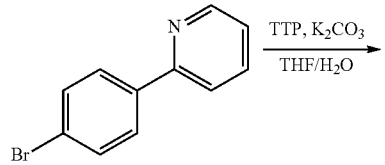

$\xrightarrow{\text{TTP, K}_2\text{CO}_3}{\text{THF/H}_2\text{O}}$

-continued

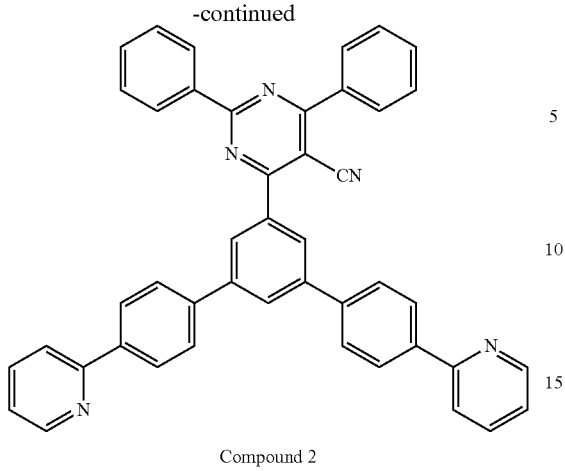

Compound 2

Compound 2B (24.4 g, 41.69 mmol) and 2-(4-bromophenyl)pyridine (19.5 g, 83.37 mmol) were put into 200 ml of tetrahydrofuran under nitrogen atmosphere, and the resulting mixture was stirred and refluxed. Thereafter, potassium carbonate (17.3 g, 125.06 mmol) was dissolved in 80 ml of water, the resulting solution was introduced thereinto, the resulting mixture was sufficiently stirred, and then tetrakis-triphenyl-phosphinopalladium (2.9 g, 2.06 mmol) was introduced thereinto. After the reaction for 5 hours, the temperature of the mixture was lowered to normal temperature and filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 2 (20.3 g, 76%).

MS: [M+H]⁺=639

Preparation Example 3. Preparation of Compound 3

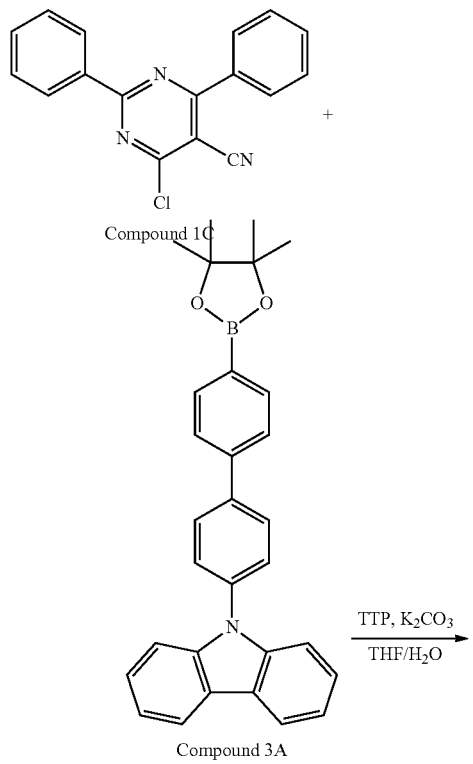

Compound 1C

Compound 3A

TTP, K₂CO₃
THF/H₂O

-continued

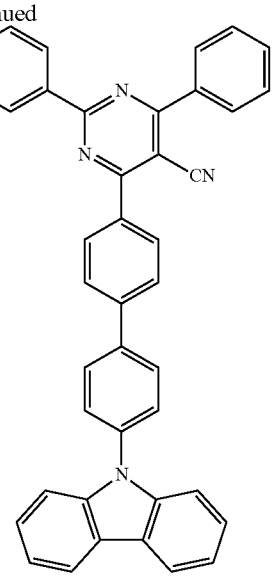

Compound 3

Compound 3 (16.0 g, yield 81%) was obtained by performing preparation in the same manner as in Preparation Example 1, except that Compound 3A was used instead of Compound 1D.

MS: [M+H]⁺=574

Preparation Example 4. Preparation of Compound 5

(1) Preparation of Compound 4A

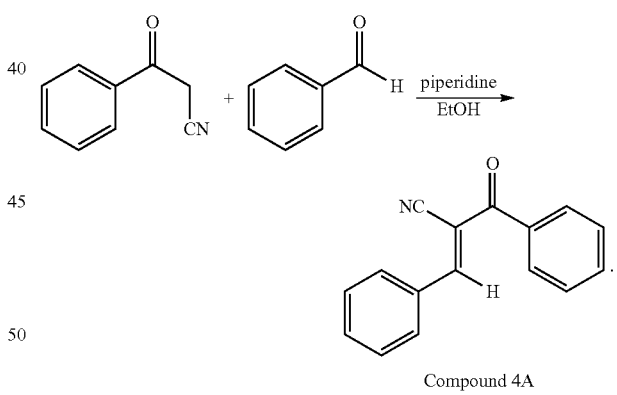

piperidine
EtOH

Compound 4A 3-oxo-3-phenylpropane nitrile (100 g, 688.90 mmol) and benzaldehyde (80.4 g, 757.58 mmol) were added to 1,000 ml of ethanol under nitrogen atmosphere, and then sufficiently stirred, and then piperidine (2.3 g, 27.56 mmol) was slowly added dropwise thereto, and then the resulting solution was refluxed and stirred for about 12 hours. After the reaction was terminated, the temperature of the mixture was lowered to normal temperature, and then filtered. The filtered material was extracted with chloroform and water, and then the organic layer was dried by using magnesium sulfate. Thereafter, the organic layer was distilled under reduced pressure, and then recrystallized with ethanol to prepare and then dry Compound 4A (123.7 g, 77%).

(2) Preparation of Compound 4B

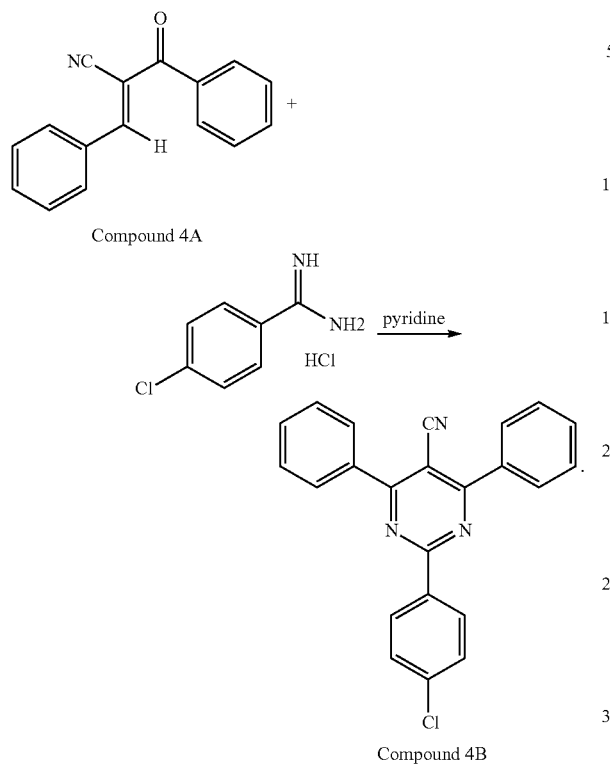

Compound 4A (50.0 g, 214.34 mmol), 4-chlorobenzimidamide hydrochloride (49.1 g, 257.21 mmol), and pyridine (0.7 g, 8.57 mmol) were put into 500 ml of ethanol, and the resulting mixture was reacted for 12 hours by being stirred and refluxed. After the reaction, the mixture was cooled to normal temperature, and then poured into 1 L of a mixed solution of water and ethanol at a ratio of 1:1 while being stirred, and then the resulting mixture was sufficiently stirred. The formed solid was filtered, and then sufficiently washed with water and hexane and then dried to prepare Compound 4B (23.7 g, 30%).

(3) Preparation of Compound 4C

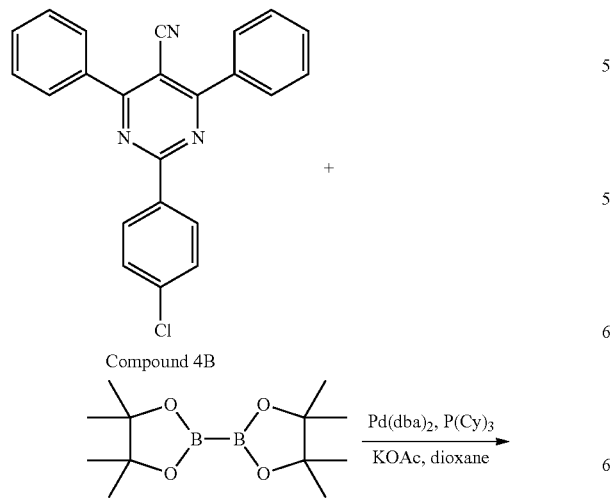

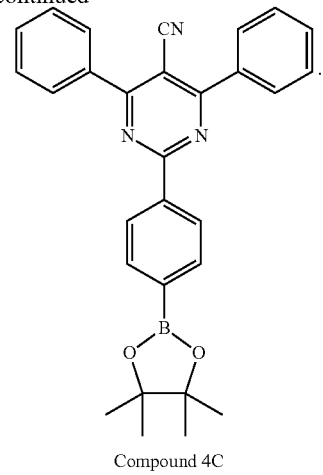

Compound 4B (23.7 g, 64.43 mmol), bis(pinacolato)diboron (18.0 g, 70.87 mmol), and potassium acetate (19.0 g, 193.29 mmol) were mixed under nitrogen atmosphere, and the resulting mixture was added to 200 ml of dioxane, and heated while being stirred. Bis(dibenzylideneacetone)palladium (1.1 g, 1.93 mmol) and tricyclohexylphosphine (1.1 mg, 3.87 mmol) were added to the mixture while being refluxed, and the mixture was refluxed and stirred for 3 hours. After the reaction was terminated, the temperature of the mixture was lowered to normal temperature, and then filtered. Water was poured into the filtrate, the product was extracted with chloroform, and the organic layer was dried with anhydrous magnesium sulfate After distillation under reduced pressure, recrystallization was performed with ethanol to prepare Compound 4C (26.0 g, 88%).

(4) Preparation of Compound 5

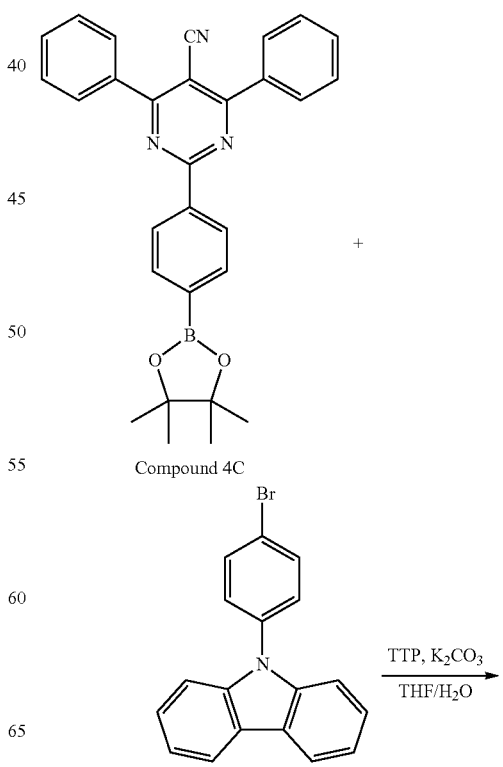

-continued

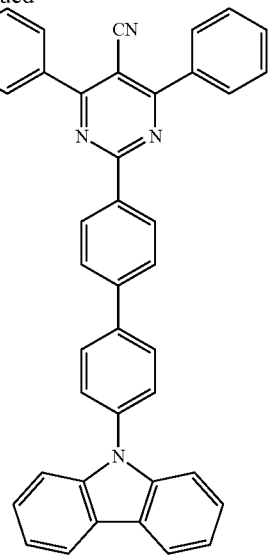

Compound 5

Compound 4C (10.0 g, 21.77 mmol) and 9-(4-bromophenyl)-9H-carbazole (7.7 g, 23.95 mmol) were put into 100 ml of tetrahydrofuran under nitrogen atmosphere, and the resulting mixture was stirred and refluxed. Thereafter, potassium carbonate (9.0 g, 65.31 mmol) was dissolved in 40 ml of water, the resulting solution was introduced thereinto, the resulting mixture was sufficiently stirred, and then tetrakis-triphenyl-phosphinopalladium (0.8 g, 0.65 mmol) was introduced thereinto. After the reaction for 12 hours, the temperature of the mixture was lowered to normal temperature and filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 5 (7.6 g, 61%).

MS: [M+H]$^+$=574

Preparation Example 5. Preparation of Compound 8

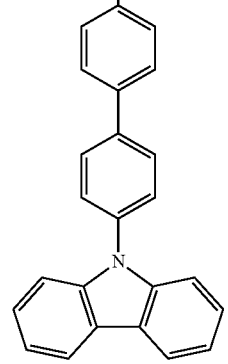

Compound 4C

-continued

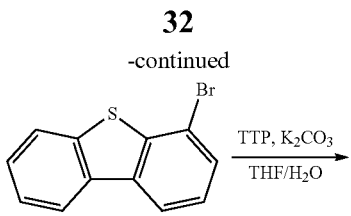

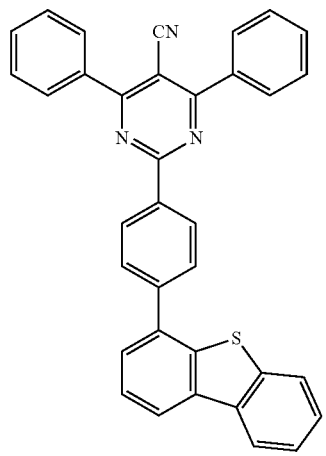

Compound 8

Compound 8 (8.8 g, yield 78%) was obtained in the same manner as in Preparation Example 4, except that 4-bromodibenzo[b,d]thiophene was used instead of 9-(4-bromophenyl)-9H-carbazole.

MS: [M+H]$^+$=515

Preparation Example 6. Preparation of Compound 9

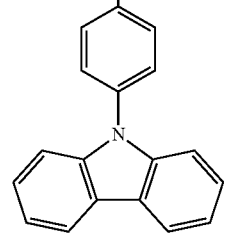

Compound 4C

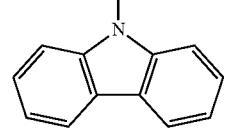

-continued

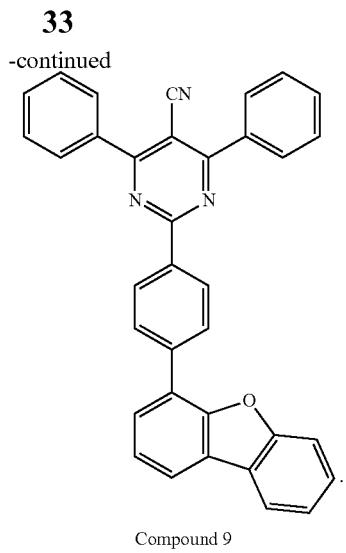

Compound 9

Compound 9 (6.9 g, yield 64%) was obtained in the same manner as in Preparation Example 4, except that 4-bromodibenzo[b,d]furan was used instead of 9-(4-bromophenyl)-9H-carbazole.

MS: $[M+H]^+$=499

Example 1

A glass substrate (Corning 7059 glass) thinly coated with ITO (indium tin oxide) to have a thickness of 1000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted repeatedly twice using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene was thermally vacuum deposited to have a thickness of 500 Å on a transparent ITO electrode, which was thus prepared, thereby forming a hole injection layer. HT1 (400 Å), which is a material transporting holes, was vacuum deposited thereon, and then the host H1 compound and the dopant D1 compound were vacuum deposited as a light emitting layer to have a thickness of 300 Å. Compound 1 prepared in Preparation Example 1 and LiQ (lithium quinolate) were vacuum deposited at a weight ratio of 1:1 on the light emitting layer, thereby forming an electron injection and transporting layer having a thickness of 350 Å. Lithium fluoride (LiF) and aluminum were sequentially deposited to have a thickness of 12 Å and 2,000 Å, respectively, on the electron injection and transporting layer, thereby forming a negative electrode. An organic light emitting device was manufactured.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

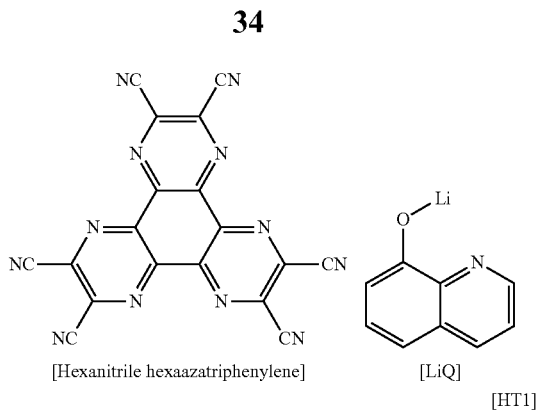

[Hexanitrile hexaazatriphenylene]   [LiQ]

[HT1]

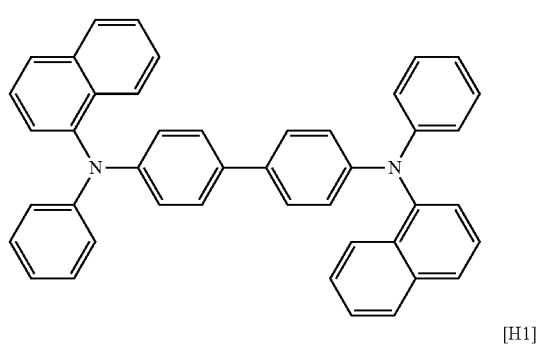

[H1]

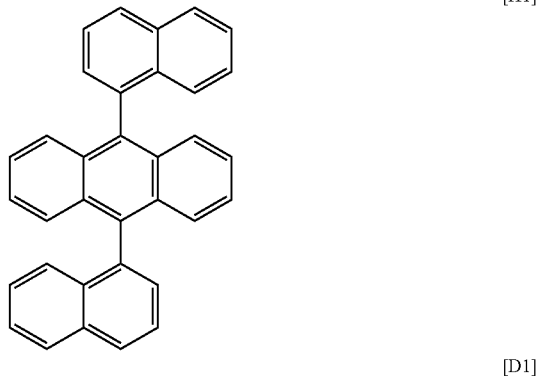

[D1]

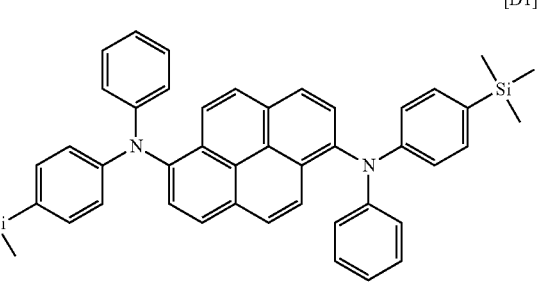

Example 2

An experiment was performed in the same manner as in Example 1, except that as the electron transporting layer, Compound 2 was used instead of Compound 1 in Example 1.

Example 3

An experiment was performed in the same manner as in Example 1, except that as the electron transporting layer, Compound 3 was used instead of Compound 1 in Example 1.

Example 4

An experiment was performed in the same manner as in Example 1, except that as the electron transporting layer, Compound 5 was used instead of Compound 1 in Example 1.

Example 5

An experiment was performed in the same manner as in Example 1, except that as the electron transporting layer, Compound 8 was used instead of Compound 1 in Example 1.

Example 6

An experiment was performed in the same manner as in Example 1, except that as the electron transporting layer, Compound 9 was used instead of Compound 1 in Example 1.

Comparative Example 1

An organic light emitting device was manufactured in the same manner as in Example 1, except that the compound of the following ET1 was used instead of Compound 1 in Example 1.

[ET1]

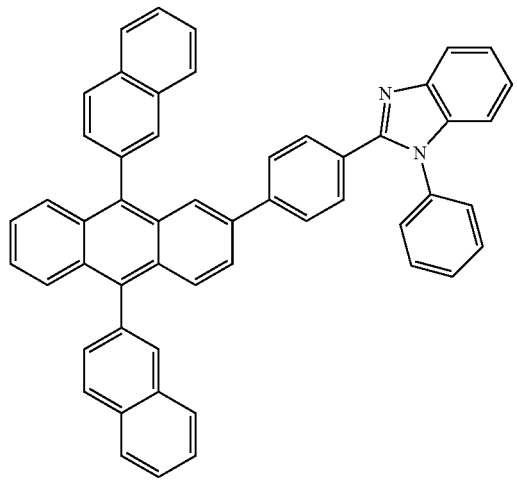

Comparative Example 2

An organic light emitting device was manufactured in the same manner as in Example 1, except that the compound of the following ET2 was used instead of Compound 1 in Example 1.

[ET2]

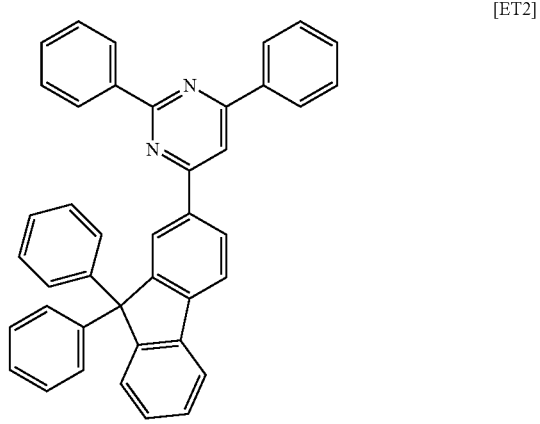 [SMILES: c1ccc(-c2cc(-c3ccc4c(c3)C(c3ccccc3)(c3ccccc3)c3ccccc3-4)nc(-c3ccccc3)n2)cc1]

Comparative Example 3

An organic light emitting device was manufactured in the same manner as in Example 1, except that the compound of the following ET3 was used instead of Compound 1 in Example 1.

[ET3]

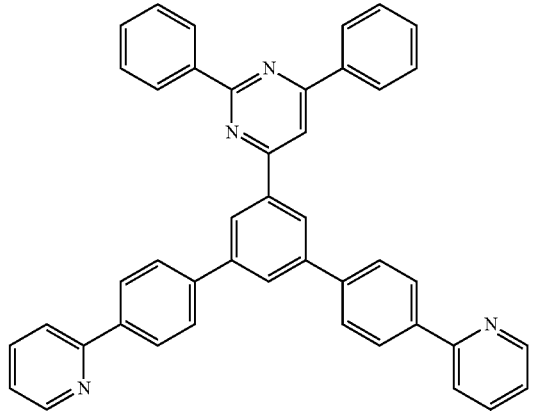

Comparative Example 4

An organic light emitting device was manufactured in the same manner as in Example 1, except that the compound of the following ET4 was used instead of Compound 1 in Example 1.

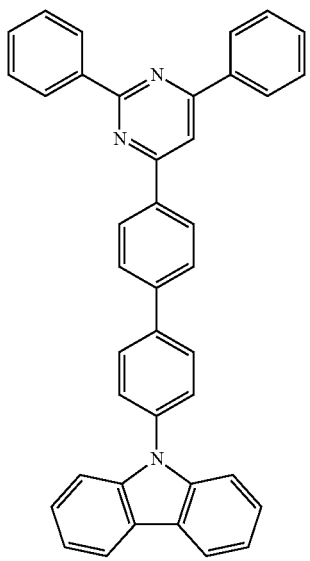

Comparative Example 5

An organic light emitting device was manufactured in the same manner as in Example 1, except that the compound of the following ET5 was used instead of Compound 1 in Example 1.

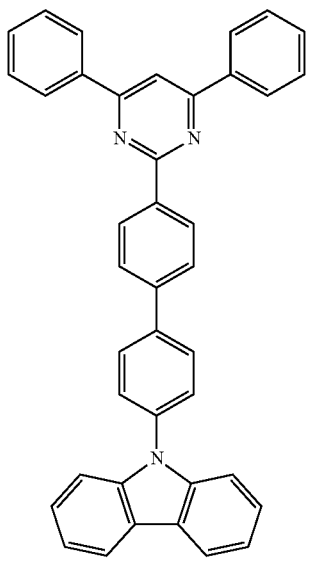

Comparative Example 6

An organic light emitting device was manufactured in the same manner as in Example 1, except that the compound of the following ET6 was used instead of Compound 1 in Example 1.

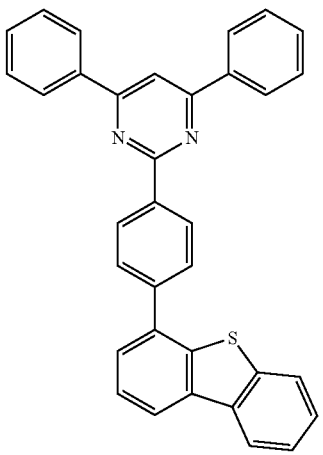

Comparative Example 7

An organic light emitting device was manufactured in the same manner as in Example 1, except that the compound of the following ET7 was used instead of Compound 1 in Example 1.

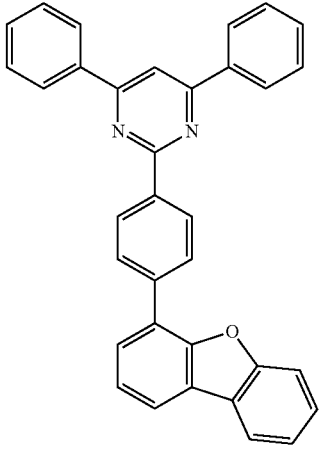

For the organic light emitting devices manufactured by using each compound as the injection and transporting layer material as in Examples 1 to 6 and Comparative Examples 1 to 7, the driving voltage and the light emitting efficiency were measured at a current density of 10 mA/cm$^2$, and a time (LT98) for reaching a 98% value compared to the initial luminance was measured at a current density of 20 mA/cm$^2$.

The results are shown in the following Table 1.

TABLE 1

| Experimental Example 10 mA/cm² | Compound | Voltage (V) | Current efficiency (cd/A) | Color coordinate (x, y) | Life Time 98 at 20 mA/cm² |
| --- | --- | --- | --- | --- | --- |
| Example 1 | Compound 1 | 4.20 | 4.98 | (0.137, 0.124) | 130 |
| Example 2 | Compound 2 | 4.33 | 4.84 | (0.139, 0.124) | 118 |
| Example 3 | Compound 3 | 4.28 | 5.01 | (0.138, 0.127) | 98 |
| Example 4 | Compound 5 | 4.44 | 4.77 | (0.138, 0.129) | 84 |
| Example 5 | Compound 8 | 4.18 | 4.98 | (0.137, 0.126) | 99 |
| Example 6 | Compound 9 | 4.15 | 5.08 | (0.137, 0.124) | 84 |
| Comparative Example 1 | ET1 | 4.00 | 5.01 | (0.132, 0.128) | 60 |
| Comparative Example 2 | ET2 | 4.11 | 5.33 | (0.138, 0.127) | 45 |
| Comparative Example 3 | ET3 | 4.00 | 5.21 | (0.139, 0.129) | 72 |
| Comparative Example 4 | ET4 | 4.05 | 4.84 | (0.137, 0.126) | 31 |
| Comparative Example 5 | ET5 | 4.15 | 4.44 | (0.140, 0.130) | 29 |
| Comparative Example 6 | ET6 | 4.10 | 5.01 | (0.139, 0.129) | 33 |
| Comparative Example 7 | ET7 | 4.15 | 5.11 | (0.139, 0.130) | 31 |

In Table 1, the case of the organic light emitting device manufactured by using the compound of the present specification as the electron injection and transporting layer material corresponds to the case where the material in the related art was used, in terms of efficiency, but exhibits excellent characteristics in terms of stability.

EXPLANATION OF REFERENCE NUMERALS AND SYMBOLS 10, 11: Organic light emitting device
20: Substrate
30: First electrode
40: Light emitting layer
50: Second electrode
60: Hole injection layer
70: Hole transporting layer
80: Electron transporting layer
90: Electron injection layer

The invention claimed is:

1. A hetero-cyclic compound of Chemical Formula 2 or 3:

Chemical Formula 2

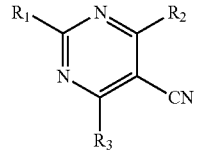

Chemical Formula 3

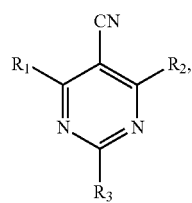

wherein:
$R_1$ and $R_2$ are an unsubstituted phenyl group, and
$R_3$ is selected from the group consisting of
a phenyl group which is substituted with a heteroaryl group,
a biphenyl group which is substituted with a heteroaryl group,
a terphenyl group which is substituted with a heteroaryl group, and
a fluorenyl group which is substituted with an aryl group.

2. The hetero-cyclic compound of claim 1, wherein the compound of Chemical Formula 4-2 is any one of the following compounds 1 to 3:

Compound 1

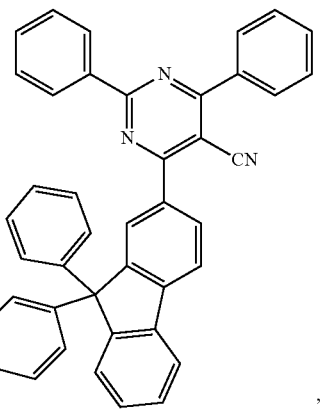

-continued

Compound 2

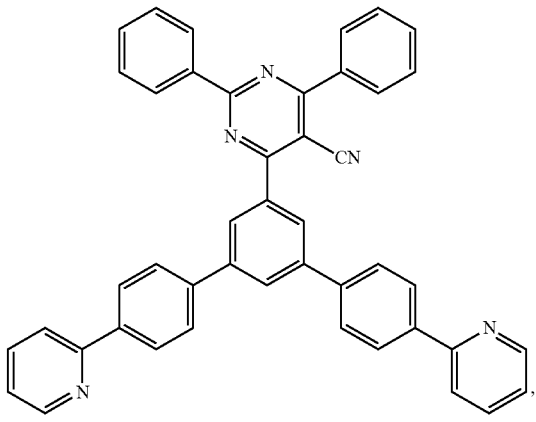

and

Compound 3

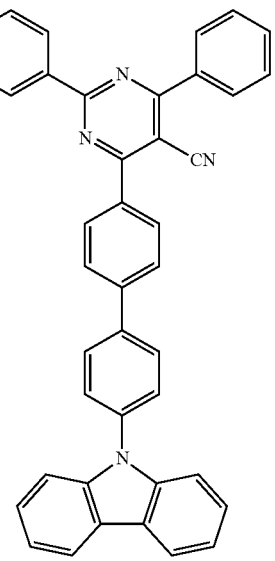

3. An organic light emitting device, comprising:
a first electrode;
a second electrode provided to face the first electrode; and
one or more organic material layers provided between the first electrode and the second electrode,
wherein one or more layers of the organic material layers comprise the hetero-cyclic compound of claim 1.

4. The organic light emitting device of claim 3, wherein the organic material layer comprises a light emitting layer, and the light emitting layer comprises the hetero-cyclic compound.

5. The organic light emitting device of claim 3, wherein the organic material layer comprises an electron transporting layer, an electron injection layer, or a layer which simultaneously transports and injects electrons, and the electron transporting layer, the electron injection layer, or the layer which simultaneously transports and injects electrons comprises the hetero-cyclic compound.

6. The organic light emitting device of claim 3, wherein the organic material layer further comprises one or more selected from the group consisting of a hole injection layer, a hole transporting layer, a light emitting layer, an electron transporting layer, and an electron injection layer.

7. The organic light emitting device of claim 3, wherein the organic material layer comprises a light emitting layer, and the light emitting layer comprises a compound represented by the following Chemical Formula 1-A:

[Chemical Formula 1-A]

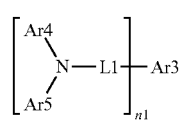

in Chemical Formula 1-A,
n1 is an integer of 1 or more,
Ar3 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L1 is a direct bond; a substituted or unsubstituted arylene group; or a substituted or unsubstituted heteroarylene group,
Ar4 and Ar5 are the same as or different from each other, and are each independently a substituted or unsubstituted aryl group; a substituted or unsubstituted silyl group; a substituted or unsubstituted alkyl group; a substituted or unsubstituted arylalkyl group; or a substituted or unsubstituted heteroaryl group, or combine with each other to form a substituted or unsubstituted ring, and
when n1 is 2 or more, two or more structures in the parenthesis are the same as or different from each other.

8. The organic light emitting device of claim 7, wherein L1 is a direct bond, Ar3 is a divalent pyrene group, Ar4 and Ar5 are the same as or different from each other, and are each independently an aryl group which is unsubstituted or substituted with a silyl group which is substituted with an alkyl group, and n1 is 2.

9. The organic light emitting device of claim 3, wherein the organic material layer comprises a light emitting layer, and the light emitting layer comprises a compound represented by the following Chemical Formula 2-A:

[Chemical Formula 2-A]

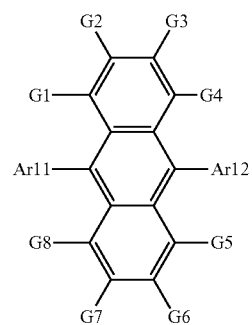

in Chemical Formula 2-A,
Ar11 and Ar12 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted monocyclic aryl group; or a substituted or unsubstituted polycyclic aryl group.

10. The organic light emitting device of claim 9, wherein Ar11 and Ar12 are a 1-naphthyl group, and G1 to G8 are hydrogen.

11. The organic light emitting device of claim 7, wherein the light emitting layer comprises a compound represented by the following Chemical Formula 2-A:

[Chemical Formula 2-A]

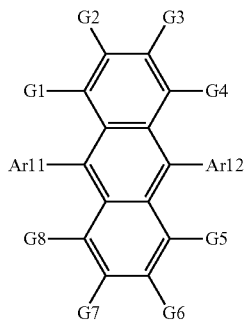

in Chemical Formula 2-A,

Ar11 and Ar12 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

12. The hetero-cyclic compound of claim 1, wherein $R_3$ is a phenyl group that is substituted with a carbazolyl group, a dibenzofuranyl group, or a dibenzothiophene group.

13. The hetero-cyclic compound of claim 1, wherein the compound of Chemical Formula 3 is any one of the following compounds 4 to 9:

Compound 4

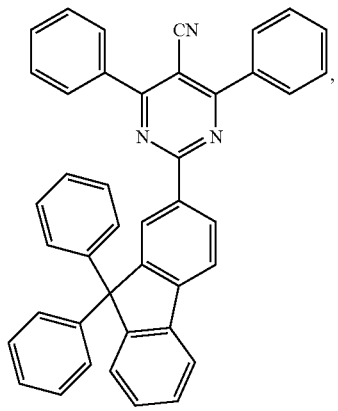

Compound 5

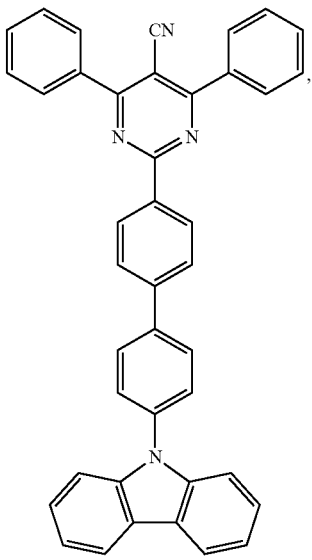

Compound 6

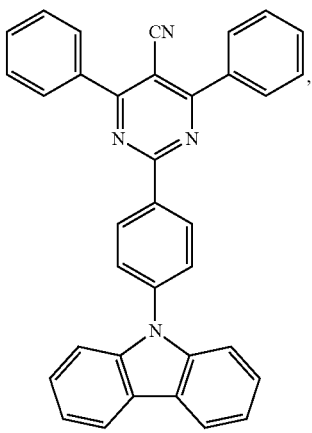

Compound 7

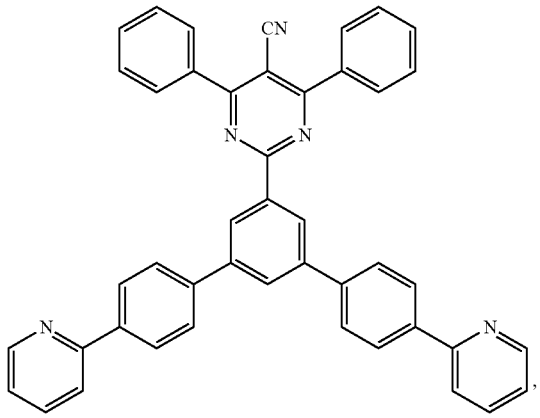

-continued
Compound 8
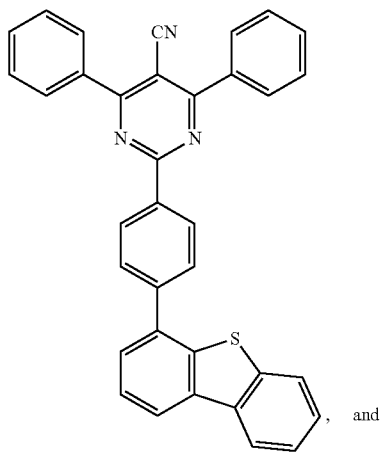
, and
Compound 9
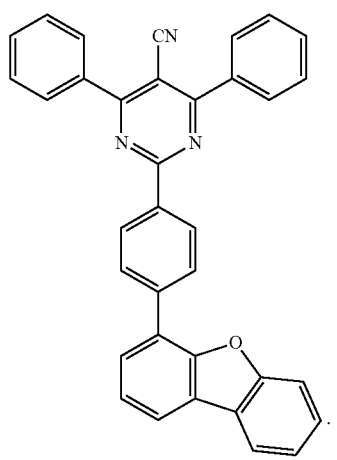
.
* * * * *